United States Patent [19]

Higgins et al.

[11] 4,317,777
[45] * Mar. 2, 1982

[54] PRODUCTION OF MALEIC ACID AND ANHYDRIDE

[75] Inventors: Raymond Higgins, Middlesbrough; Graham J. Hutchings, Northallerton, both of England

[73] Assignee: Imperial Chemical Industries Limited, London, England

[*] Notice: The portion of the term of this patent subsequent to Sep. 16, 1997, has been disclaimed.

[21] Appl. No.: 138,318

[22] Filed: Apr. 8, 1980

Related U.S. Application Data

[63] Continuation-in-part of Ser. No. 6,554, Jan. 25, 1979, Pat. No. 4,222,945.

[30] Foreign Application Priority Data

Jan. 30, 1978 [GB] United Kingdom ................. 3686/78
Feb. 6, 1978 [GB] United Kingdom ................. 4657/78
Nov. 20, 1978 [GB] United Kingdom ............... 45295/78

[51] Int. Cl.$^3$ .......................................... C07D 307/60
[52] U.S. Cl. ................................................. 260/346.75
[58] Field of Search ................................... 260/346.75

[56] References Cited

U.S. PATENT DOCUMENTS 3,862,146  1/1975  Boghosian ..................... 260/346.75
4,017,521  4/1977  Schneider ...................... 260/346.75
4,222,945  9/1980  Higgins et al. ................. 260/346.75

Primary Examiner—Henry R. Jiles
Assistant Examiner—Bernard Dentz
Attorney, Agent, or Firm—Cushman, Darby & Cushman

[57] ABSTRACT

Hydrocarbons, particularly n-butane, are oxidized to acid anhydrides, especially maleic anhydride, by contacting them at concentrations above the flammable limit with oxygen in the presence of a vanadium/phosphorus mixed oxide catalyst having a surface area of at least 10 m$^2$/g. The concentration of inert gas is more than 70 molar percent and the oxygen concentration is greater than 13 molar percent.

6 Claims, No Drawings

4,317,777

PRODUCTION OF MALEIC ACID AND ANHYDRIDE

CROSS-REFERENCE TO RELATED APPLICATIONS

This application is a continuation-in-part of our earlier application Ser. No. 6,554 filed Jan. 25, 1979 and now U.S. Pat. No. 4,222,945.

This invention relates to the production of carboxylic acid anhydrides and catalysts therefor.

The invention comprises producing a carboxylic acid anhydride by oxidising a hydrocarbon which comprises at least 4 linear carbon atoms, for example a hydrocarbon having the formula R'CH$_2$CH$_2$CH$_2$CH$_2$R'' where R' and R'' are individually hydrogen or alkyl groups having together at most 6 and preferably at most 4 carbon atoms, an alkene or alkadiene corresponding thereto, a cycloalkane having a —CH—CH$_2$—CH$_2$—CH— group preferably in a ring, for example cyclohexane, or benzene or orthoxylene or naphthalene, by contacting the hydrocarbon with oxygen, the hydrocarbon concentration being higher than the flammable limit, the oxygen concentration being greater than 13 and preferably greater than 14 and preferably at most 20, for example 14–20 molar percent of the total material fed to the reaction and/or the concentration of any inert gas present being less than 70 molar percent of the total material fed to the reaction; in the presence of a catalyst which comprises a phosphorus/vanadium mixed oxide, the atomic ratio of vanadium to phosphorus being in the range of 0.5:1 to 2:1, the surface area of the catalyst being at least 10 sq. meters per gram, preferably at least 15 sq. meters per gram and more preferably at least 30 sq. meters per gram.

The concentration of the hydrocarbon is preferably greater than 8.5 molar percent and more preferably greater than 10 molar percent of the total material fed to the reaction.

The process is suitably carried out at a temperature in the range 250°–600° C. and more preferably 300°–400° C. It may be carried out at a pressure of 0.5–20 bars absolute and more preferably 1–3 bars absolute.

Inert materials, for example carbon monoxide, carbon dioxide, nitrogen or argon may be present. Other materials may be present for examples as a consequence of combustion or as impurities in the hydrocarbon or oxygen fed to the process. Inert materials and/or such other materials may build up in the system if the hydrocarbon is recycled to the process after partial conversion.

If the hydrocarbon is orthoxylene or naphthalene, the carboxylic acid anhydride produced in the process is phthalic anhydride; in most other cases it is maleic anhydride. The process is particularly attractive in the production of maleic anhydride because high selectivities to maleic anhydride based on hydrocarbon converted may be obtained by operation at low conversions for example total conversions of 10 to 50% and preferably 10 to 30% of the hydrocarbon, because, even at low conversions of the high concentrations of hydrocarbon present in the invention the reaction product may contain a substantial content of maleic anhydride and a substantial yield of maleic anhydride may therefore be recovered from the reaction product by condensation. Further maleic anhydride may be recovered by solvent stripping and/or water washing.

In the production of maleic anhydride it is preferred that the hydrocarbon should comprise n-butene, butadiene or preferably n-butane; for example it may be a mixture of hydrocarbons containing n-butane for example naphtha or a mixture of butanes but it is preferred that the feedstock should be substantially n-butane itself.

The hydrocarbon may be readily recovered for recycle by known means for example condensation, stripping or adsorption. It is preferred however to carry out the reaction using substantially pure oxygen and to operate the process by recovering the product, and recycling unconverted hydrocarbon together with carbon monoxide and carbon dioxide produced in the process to the reaction whilst purging an appropriate proportion of the recycle stream in order to limit the build up of inert materials in the process. The purge may be treated for the recovery of its hydrocarbon content or may for example be used as a fuel.

Suitable catalysts for the process may have an atomic ratio of vanadium to phosphorus in the range 1:0.8 to 1:1.7 and may, if desired, include a promoter for example nickel, cadmium, zinc, bismuth, lithium, copper, molybdenum, uranium, zirconium, hafnium, chromium, iron, magnesium, manganese or preferably cobalt or a rare earth metal for example cerium or lanthanum. The atomic ratio of the promoter to vanadium may be for example 0.001:1 to 1:1.

The surface area of the catalyst may be for example 10 to 100 sq. meters per gram and preferably 15 to 100 sq. meters per gram and more preferably 30 to 80 sq. meters per gram. It may be prepared by reacting a vanadium compound with a phosphorus acid in a suitable solvent for example a strong aqueous acid for example HCl, precipitating a vanadium/phosphorus mixed oxide catalyst precursor preferably by removing solvent (preferably at least 90% and more preferably at least 95% of the solvent being removed), preferably leaving a dry or nearly dry solid, preferably extracting the precursor with water or another solvent for the phase identified by G. Ladwig in Z. CHEM. 1968 volume 8, pages 307 and 308 as a vanadium hydrogen phosphate without strong hydrogen bonding of formula VO(H$_2$PO$_4$)$_2$ (which we refer to as phase E), for example dimethylsulphoxide, until substantially only material substantially insoluble in water or the said solvent is left and converting the said precursor to a catalytically active form by heating. A phase transition for example to the beta form as disclosed in U.S. Pat. No. 3,864,208 or to a high area form of the αVPO$_5$ identified by Jordan and Calvo in Canadian Journal of Chemistry 51 2621-5 (1973) in terms of its X-ray diffraction characteristics and herein referred to as phase X, is believed to occur during the heating.

It is preferred that the mean crystallite size of the extracted precursor should be at most 1000 Å, preferably at most 500 Å and more preferably at most 300 Å for example in the range 100–300 Å. It is found that catalysts prepared from such crystallites have a particularly high activity and are especially suitable for use in the process. Crystallites of such size may be produced by comminuting, suitably by ball milling in the presence of a suitable solvent for example an aliphatic hydrocarbon e.g. cyclohexane until the desired crystallite size is reached preferably in the presence of a dispersant. Precursors of the appropriate crystallite size may be formed into pellets with a suitable pelletising agent and calcined in the pelletised form if desired.

It is believed that vanadium/phosphorus mixed oxide catalysts prepared by heating catalyst precursors which have a mean crystallite size of at most 1000 Å are novel. Such catalysts may be as hereinbefore described. A promoter may suitably be introduced to the catalyst by coprecipitation with the vanadium/phosphorus mixed oxide, by impregnation of the precursor with a solution of the promoter before or after pelletising or after conversion to the catalytically active form by heating.

The mean crystallite size of the catalyst precursor may be estimated by the breadth at half scale height of characteristic X-ray diffraction lines.

If desired catalysts for use in this invention may comprise supports, in which case the surface area is defined as that of the catalyst similarly prepared but without a support, or may comprise reinforcing agents for example, silica introduced as a suitable solution.

Suitable supports include alumina, silica, titania, or silicon carbide.

EXAMPLE 1

Vanadium pentoxide (121.3 g) and concentrated aqueous hydrochloric acid (1520 mls) were refluxed with stirring for about 1 hour to give a blue solution. To this solution orthophosphoric acid (88%, 178.2 g) was added and the resulting solution was refluxed for a further period of about 1 hour. The solution was then evaporated to dryness and the resulting solid was dried in an oven at 110° C. The P:V ratio of this precursor was 1.2:1. The resulting solid was then boiled with water (20 mls/g solid) for 3 hours and the resulting blue suspension was filtered hot, washed with a small amount of warm water and dried in air at 60° C. A portion of the dried solid was then ball milled in cyclohexane in the presence of 2% by weight of the catalyst of an organic comb graft copolymer [poly-12-hydroxystearic acid (molecular weight about 1800)/ethyl acrylate/dimethyl aminoethyl methacrylate:50/45/5] for 150 hours using high density alumina spheres (density=3.5 gm/cc). The organic comb graft copolymer is a product of copolymerising the condensate of one mole of poly-12-hydroxystearic acid of molecular weight about 1800 with one mole of glycidyl methacrylate, with ethyl acrylate and dimethyl amino ethyl methacrylate in the ratio of 50:45:5 by weight). After ball milling the cyclohexane solvent was then removed by evaporation and the resulting grey solid was dried at 110° C. The mean crystallite size of the precursor after ball milling was found to be 250 Å as measured by X-ray diffractiometry. A portion of the ball milled precursor was mixed with a pelleting agent sold under the trade name "Sterotex" (2% by weight) and pelletised under a pressure of 16 tons in $^{-2}$. The pellet was then crushed and sieved to give particles 500–700μ in size. A 5 ml portion was charged to a tubular fixed bed reactor and the catalyst was calcined in situ by heating to 385° C. at a rate of 9° C./min whilst 1.5% v/v n-butane in air flowed through the bed at a gas hourly space velocity (GHSV) of 1000 hr$^{-1}$. After 110 hours time on line with a butane feed concentration of 14 mole % and an inlet oxygen concentration of 18.1 mole % (remainder inerts) at a reactor temperature of 360° C. and GHSV of 1100 hr$^{-1}$ the catalyst gave an n butane conversion of 17% and a selectivity to maleic anhydride of 78 mole %. The surface area of the final catalyst was 35 m$^2$/g.

EXAMPLE 2

A catalyst precursor was prepared, boiled with water, washed, dried, ball milled, pelleted, crushed and sieved to give particles 500–700μ in size as described in Example 1. The crystallite size of the catalyst precursor after ball milling was about 250 Å. The particles were dried for 15 hours at 148° C. and were then impregnated with an isobutanol solution (containing 14 g. per 100 ml) of lanthanum nitrate (as La(NO$_3$)$_3$.6H$_2$O) to give a catalyst with a La:V ratio of 0.02:1. After drying a 5.0 ml portion was charged to a tubular fixed bed reactor and the catalyst was calcined in situ by heating to 385° C. at a rate of 9° C./min whilst a 1.5% v/v n-butane/air mixture flowed through the bed at a gas hourly space velocity (GHSV) of 1000 hr$^{-1}$. After 210 hours time on line with a butane feed concentration 15.2 mole % and an inlet oxygen concentration of 17.8 mole % (remainder inerts) at a reactor temperature of 340° C. and a GHSV of 1000 hrs$^{-1}$ the catalyst gave a butane conversion of 13% and a selectivity to maleic anhydride in excess of 75 mole %. The surface area of the final catalyst was 51 m$^2$/g.

EXAMPLE 3

Vanadium pentoxide (60.6 g) and concentrated aqueous hydrochloric acid (790 mls) were heated with stirring for about 1 hour to give a blue solution. To this solution orthophosphoric acid (88%, 89.1 g) was added and the resulting solution was refluxed for a further period of about 2 hours. The solution was then evaporated by distillation to about 200 mls. 200 mls of concentrated aqueous hydrochloric acid were added, the resulting solution was refluxed for a further period of 1 hour and the solution was then evaporated to dryness and the resulting solid was dried in an oven at 110° C. The P:V ratio of this catalyst precursor was 1.2:1. The resulting solid was then boiled with water (20 mls/g solid) for 2 hours and the resulting blue suspension was filtered hot, washed with a small amount of warm water and dried in air at 60° C. A portion of the dried solid was then mixed with molybdenum trioxide (MoO$_3$) so that the V:Mo atomic ratio was 1:0.025. The resulting solid was then ball milled, pelleted, crushed and sieved to give particles 500–700μ in size as described in Example 1. The crystallite size of the catalyst precursor after ball milling was 450 Å. A 5.0 ml portion was charged to a tubular fixed bed reactor and the catalyst was calcined in situ by heating to 385° C. at a rate of 9° C./min whilst a 1.5% v/v n-butane/air mixture flowed through the bed at a GHSV of 1000 hr$^{-1}$. After 480 hours time on line at an n-butane feed concentration of 14 mole % and an inlet oxygen concentration of 18.1 mole % (remainder inerts) at a reactor temperature of 360° C. and a GHSV of 2000 hr$^{-1}$ the catalyst gave an n-butane conversion of 12% and a selectivity to maleic anhydride of 73 mole %. The surface area of the final catalyst was 32 m$^2$/g.

EXAMPLE 4

A catalyst precursor was prepared, washed with water and dried as described in Example 3. The solid was then mixed with cerous nitrate (as Ce(NO$_3$)$_3$.6H$_2$O) so that the V:Ce atomic ratio was 1:0.005. The resulting solid was then ball milled, pelleted, crushed and sieved to give particles 500–700μ in size as described in Example 1. The crystallite size of catalyst precursor after ball milling was about 300 Å. A 5.0 ml portion was charged to a tubular fixed bed reactor and the catalyst was calcined in situ by heating to 385° C. at a rate of 9° C./min whilst 1.5% v/v n-butane/air flowed through the bed at a GHSV of 1000 hr$^{-1}$. After 205 hours time on line at an n butane feed concentration of 15.9 mole % and an inlet oxygen concentration of 17.7 mole % (remainder inerts) at a reactor temperature of 360° C. and a GHSV of 2260 hr$^{-1}$ the catalyst gave an n-butane conversion of 13.8% and a selectivity to maleic anhydride of 71 mole %. The surface area of the final catalyst was 27 m$^2$/g.

EXAMPLE 5

A vanadium phosphorus mixed oxide catalyst precursor promoted by cobalt chloride was prepared as described in U.S. Pat. No. 3,987,063 Example 2. The V:P:Co atomic ratio of the catalyst precursor prepared was 1:1.2:0.19 and the mean crystallite size of the precursor was <1000 Å and was typically 1-5μ. A portion of the precursor was mixed with a pelleting agent sold under the trade name "Sterotex" (2% by weight) and pelletised under a pressure of 16 tons in $^{-2}$. The pellet was then crushed and sieved to give particles 500-710μ in size and a portion (5.0 mls) was charged to a tubular fixed bed reactor and the catalyst was calcined in situ by heating to 385° C. at a rate of 9° C./min whilst a 1.5% v/v n-butane/air mixture flowed through the bed at a GHSV of 1000 hr$^{-1}$. After 18 hours the temperature was raised to 410° C. and then decreased to 385° C. after 48 hours. After 680 hours time on line and with a butane feed concentration of 13 mole % and an inlet oxygen concentration of 18.3 mole % (remainder inerts) at a reactor temperature of 340° C. and a GHSV of 200 hr$^{-1}$ the catalyst gave a butane conversion of 22% and a selectivity to maleic anhydride in excess of 75 mole %. The surface area of the final catalyst was 20 m$^2$/g.

EXAMPLE 6

Vanadium pentoxide (60.6 g) and concentrated aqueous hydrochloric acid (790 mls) were heated with stirring from about 2 hours to give a dark blue solution. To this solution orthophosphoric acid (89.1 g, 88%) was added and the resulting solution was refluxed for a further period of about 2 hours. The solution was then evaporated to dryness and the resulting solid was dried in an air oven at 150° C. The resulting solid was then boiled in water (20 mls/g solid) for about 1 hour and filtered hot, washed with a small amount of warm water and dried at 150° C. in an air oven. The mean crystallite size of the catalyst precursor was >1000 Å and was typically >1μ. A portion of the dried solid was pelleted, crushed and sieved to give particles 500-710μ in size as described in Example 2. The particles were then dried at 150° C. for 16 hours and were then impregnated with an isobutanol solution (containing 14 g per 100 mls) of lanthanum nitrate (as La(NO$_3$)$_3$.6H$_2$O) to give a catalyst with a La:V atomic ratio of 0.02:1. After drying a 5.0 ml portion was charged to a tubular fixed bed reactor and the catalyst was calcined in situ by heating to 385° C. at a rate of 9° C./min whilst a 1.5% v/v n-butane/air mixture flowed through the bed at a GHSV of 1000 hr$^{-1}$. After 139 hours time on line with a butane feed concentration of 16 mole % and an inlet oxygen concentration of 17.6 mole % (remainder inerts) at a reactor temperature of 340° C. and a GHSV of 1000 hr$^{-1}$ the catalyst gave a butane conversion of 11.8% and a selectivity to maleic anhydride of 76 mole %. The surface area of the final catalyst was 16 m$^2$/g. The final catalyst was examined by X ray diffractiometry and was found to exhibit the characteristic X ray powder diffraction pattern of phase X listed in Table 1. By analysis of the peak areas it was found that about 30% phase X was present in the catalyst.

TABLE 1

X ray powder diffraction of phase X
d (Å) spacings were obtained using CuKα radiation
Only lines from spacing between 4.44Å and 1.83Å were measured

| 2θ | d(Å) | Relative** Intensity |
|---|---|---|
| 20.0 | 4.44 | <1 |
| 21.0 | 4.24 | <1 |
| 24.9 | 3.57 | 6 |
| 29.1 | 3.07 | 5 |
| 29.8 | 3.00 | 10 |
| 39.2 | 2.30 | <1 |
| 40.7 | 2.22 | <1 |
| 42.7 | 2.12 | <1 |
| 46.1 | 1.97 | 1 |
| 47.9 | 1.90 | 1 |
| 49.9 | 1.83 | 1.5 |

**Intensities normalised to reflection at 2θ = 29.8° being 10.

Examples 7-10 demonstrate that the catalysts of the invention can be used to oxidise n-butane to maleic anhydride under "fuel lean" conditions.

EXAMPLE 7

A catalyst precursor was prepared, boiled with water, washed with warm water, dried, ball milled in the presence of a solvent and dispersant, dried, pelleted, crushed and sieved to give particles 500-700μ in size as described in Example 1. After ball milling as described in Example 1 the catalyst precursor had a mean crystallite size of about 250 Å as measured by X ray diffractiometry. The particles were then calcined at 400° C. for 16 hours in a flowing atmosphere of nitrogen. A 4.2 ml portion of the calcined particles was then charged to a tubular fixed bed reactor and the catalyst was heated to 385° C. at a rate of 9° C./min whilst an n-butane/air mixture flowed through the catalyst bed at a GHSV of 1000 hr$^{-1}$. After 117 hours time on line with a butane feed concentration of 1.5 mole % in air at a reactor temperature of 420° C. and GHSV of 1000 hr$^{-1}$ the catalyst gave a 51 mole % of maleic anhydride at an n-butane conversion of 96%. At a reactor temperature of 420° C. and a GHSV of 4000 hr$^{-1}$ the catalyst gave a 42 mole % pass yield of maleic anhydride at an n-butane conversion of 62%. The surface area of the final catalyst was 46 m$^2$/g.

EXAMPLE 8

A catalyst promoted with lanthanum (V:La atomic ratio=1:0.02) was prepared as described in Example 2. The crystallite size of the catalyst precursor after ball milling was about 250 Å. A 4.0 ml portion of the catalyst was charged to a tubular fixed bed reactor and the catalyst was calcined in situ by heating to 385° C. at a rate of 9° C./min whilst n-butane/air mixture flowed through the catalyst bed at GHSV of 1250 hr$^{-1}$. After 130 hours time on line with an n-butane feed concentration of 1.5 mole % in air at a reactor temperature of 420° C. and a GHSV of 5000 hr$^{-1}$ the catalyst gave a 47 mole % pass yield of maleic anhydride at an n-butane conversion of 81% (activity=1.47 moles maleic anhydride per liter catalyst/hour). The surface area of the final catalyst was 40 m$^2$/g.

EXAMPLE 9

The catalyst promoted with cerium (V:Ce atomic ratio = 1:0.005) prepared and calcined as stated in Example 4 was used in oxidise n-butane to maleic anhydride under "fuel lean" conditions. The crystallite size of the catalyst precursor after ball milling was about 300 Å. After 183 hours time on line with a feed concentration of n-butane of 1.5 mole % in air at a reactor temperature of 420° C. at a GHSV of 3100 hr$^{-1}$ the catalyst gave a 49 mole % pass yield of maleic anhydride at an n-butane conversion of 89%.

EXAMPLE 10

The catalyst promoted with molybdenum (V:Mo = 1:0.025) prepared and calcined as described in Example 3 was used to oxidise n-butane to maleic anhydride under "fuel lean" conditions. The crystallite size of the catalyst precursor after ball milling was about 450 Å. After 109 hours time on line with a feed concentration of 1.5% n-butane in air at a reactor temperature of 420° C. and a GHSV of 3000 hr$^{-1}$ the catalyst gave a pass yield of maleic anhydride of 60% at an n-butane conversion of 94%.

Examples 11-13 demonstrate that amines and surfactant molecules can be used as dispersants during the comminution process in place of the organic comb graft copolymer described previously.

EXAMPLE 11

A catalyst precursor was prepared, boiled with water, washed with warm water and dried as described in Example 1. A portion of the dried solid was then ball milled in cyclohexane in the presence of 2% by weight of the catalyst of oleylamine for 150 hours using high density alumina spheres (density = 3.5 gm/cc). After ball milling the cyclohexane solvent was removed by evaporation and the resulting solid was dried at 110° C. The mean crystallite size of the precursor after ball milling was found to be about 400 Å as measured by X ray diffractiometry. A portion of the ball milled precursor was then pelleted, crushed and sieved to give particles 500-700$\mu$ in size as described in Example 1. A 5 ml portion was charged to a tubular fixed bed reactor and the catalyst was calcined in situ by heating to 385° C. at 9° C./min whilst an n-butane/air mixture flowed through the bed at a GHSV of 1000 hr$^{-1}$. After about 100 hours time on line with a butane feed concentration of 1.5 mole % in air at a reactor temperature of 420° C. and a GHSV of 1850 hr$^{-1}$ the catalyst gave a pass yield of maleic anhydride of 49% at an n-butane conversion of 93%. The surface area of the final catalyst was 34 m$^2$/g.

EXAMPLE 12

A catalyst was prepared and calcined as described in Example 11 except that the catalyst precursor was ball milled in cyclohexane in the presence of 2% by weight of the catalyst of n-octylamine. The mean crystallite size of the ball milled precursor was found to be about 400 Å by X ray diffractiometry. After 115 hours time on line with an n-butane feed concentration of 1.5 mole % in air at a reactor temperature of 420° C. and a GHSV of 3000 hr$^{-1}$ the catalyst gave a pass yield of 60 mole % at an n-butane conversion of 95%. The surface area of the final catalyst was 46 m$^2$/g.

EXAMPLE 13

A catalyst was prepared and calcined as described in Example 11 except that the catalyst precursor was milled in cyclohexane in the presence of 2% by weight of the catalyst of cetyl trimethyl ammonium bromide. The mean crystallite size of the ball milled precursor was found to be about 300 Å by X ray diffractiometry. After 140 hours time on line with an n-butane feed concentration of 1.5 mole % in air at a reactor temperature of 420° C. and a GHSV of 2800 hr$^{-1}$ the catalyst gave a pass yield to maleic anhydride of 51 mole % at an n-butane conversion of 86%. The surface area of the final catalyst was 42 m$^2$/g.

EXAMPLE 14

This Example demonstrates that comminution of vanadium phosphorus mixed oxide catalyst precursors increases the surface area even when dispersant molecules are not used, but that improved surface areas can be achieved when suitable dispersants are used.

A catalyst precursor was prepared, boiled in water, washed with warm water and dried as described in Example 1. The following comminution experiments were carried out:

Sample 1: a portion of the dried catalyst precursor was ball milled in cyclohexane in the absence of any dispersant for 150 hours using high density alumina spheres (density = 3.5 g/cc). The cyclohexane solvent was then removed by evaporation and the resulting solid was dried at 110° C.

Sample 2: a portion of the dried catalyst precursor was ball milled in cyclohexane in the presence of 2% by weight of the catalyst of the organic comb graft copolymer (poly-12-hydroxystearic acid (molecular weight about 1800)/ethyl acrylate/dimethylamino ethyl methacrylate:50/45/5) prepared as described in Example 1, for 150 hours using high density alumina balls (density = 3.5 g/cc). The cyclohexane solvent was then removed by evaporation and the resulting solid was dried at 110° C.

Sample 3: a portion of the dried catalyst precursor was ball milled and dried as described for Sample 2 except that the organic comb graft copolymer is: poly-12-hydroxy stearic acid (molecular weight about 1800)/ethyl acrylate/glycidyl methacrylate:50/47.5/2.5. The organic comb graft copolymer is a product copolymerising the condensate of one mole of poly-12-hydroxystearic acid (acid value 32, molecular weight about 1800) with one mole of glycidyl methacrylate, with ethyl acrylate and glycidyl methacrylate in the ratio 50/47.5/2.5 by weight.

Sample 4: a portion of the dried catalyst precursor was ball milled and dried as described for Sample 2 except that the organic comb graft copolymer is: poly-12-hydroxy stearic acid (molecular weight about 1800)/styrene/hydroxy ethyl methacrylate:50/25/25. The organic comb graft copolymer is a product of copolymerising the condensate of one mole of poly-12-hydroxystearic acid (acid value 32, molecular weight about 1800) with one mole of glycidyl methacrylate, with styrene and hydroxy ethyl methacrylate in the ratio 50/25/25 by weight.

The surface area and the mean crystallite size of the ball milled samples 1, 2, 3, 4 were then measured. The samples were then calcined at 400° C. for 12 hours in a muffle furnace and the surface areas and the mean crystallite sizes were again measured. The results are given in the Table below. The mean crystallite size of the catalyst precursor before comminution was >1000 Å, typically 5 and the surface area was 1 m²/g before and 5 m²/g after calcination at 400° C. for 12 hours.

TABLE 2

| Sample No | Before Calcination | | After Calcination at 400° C., 12 hours | |
|---|---|---|---|---|
| | Surface Area (m²/g) | Mean Crystallite Size (Å) | Surface Area (m²/g) | Mean Crystallite Size (Å) |
| 1 | 7 | 400 | 9 | 150 |
| 2 | 2 | 250 | 20 | 170 |
| 3 | 14 | 250 | 16 | 150 |
| 4 | 8 | 400 | 11 | 150 |

COMPARATIVE EXAMPLE

A vanadium phosphorus mixed oxide catalyst precursor was prepared using the method described in West German Pat. No. 2,256,909 Examples 1–12. The mean crystallite size of the catalyst precursor was >1000 Å and was typically 1 to 5μ. A portion of the catalyst precursor was pelleted, crushed and sieved to give particles 500–700μ n size as described in Example 1. A 5.0 ml portion of the particles were then charged to a tubular fixed bed reactor. The catalyst was then calcined in situ by heating to 385° C. whilst n-butane/air mixture flowed through the catalyst bed at a GHSV of 1000 hr$^{-1}$. After 100 hours the temperature was raised to 450° C. for 1 hour and then lowered to 425° C. for 5 hours. The butane feed concentration was 1.5 mole % in air. At a reactor temperature of 425° C. and a GHSV of 500 hr$^{-1}$ the catalyst gave a pass yield to maleic anhydride of 20 mole % at an n-butane conversion of 34%. The surface area of the final catalyst was 3 m²/g.

EXAMPLE 15

A vanadium phosphorus mixed oxide catalyst was prepared in the absence of hydrochloric acid essentially as described in U.S. Pat. No. 4,116,868 Example 1. Vanadium pentoxide (227.8 g), orthophosphoric acid (88%, 152.8 g), phosphorous acid (97.6%, 116 g) and water (775.2 g) were mixed in a glass tube and sealed. The tube was then heated in an autoclave to 145° C. for 4 hours and was then allowed to cool to room temperature. A blue precipitate was observed in suspension in a blue liquid. The precipitate was recovered by filtration and dried in air at 110° C. The mean crystallite size of the precursor was >1000 Å and was typically >1μ. A portion of the precursor was mixed with a pelleting agent sold under the trade name "STEROTEX" (3% by weight) and pelletised under a pressure of 27 tons in $^{-2}$. The pellet was then crushed and sieved to give particles 500–700μ in size and a portion (5.0 mls) was charged to a tubular fixed bed reactor and the catalyst was calcined in situ by heating to 385° C. at a rate of 9° C./min. whilst a 1.5% v/v n-butane/air mixture flowed through the bed at a GHSV of 1000 hr$^{-1}$. After 48 hours time on line the reactor temperature was increased to 400° C. and subsequently after 118 hours time on line to 420° C. After 166 hours the feed was changed to a butane feed concentration of 16.7 mole % and an inlet oxygen concentration of 17.5 mole % (remainder inerts). At a reactor temperature of 360° C. and GHSV of 1000 hr$^{-1}$ the catalyst gave a butane conversion of 12.2% and a selectivity to maleic anhydride of 78 mole %. The surface area of the final catalyst was 18.7 m²/g.

EXAMPLE 16

A catalyst precursor was prepared and dried as described in Example 15. A portion of the dried solid was then ball milled in cyclohexane in the presence of 2% by weight of the catalyst of an organic comb graft copolymer (poly-12-hydroxystearic acid (molecular weight about 1800)/ethyl acrylate/glycidyl methacrylate:50/47.5/2.5) for 150 hours using high density alumina spheres (density=3.5 gm/cc). The organic comb graft copolymer as a product of copolymerising the condensate of 1 mole of poly-12-hydroxystearic acid (acid value 32, molecular weight about 1800) with one mole of glycidyl methacrylate, with ethyl acrylate and glycidyl methacrylate in the ratio 50/47.5/2.5 by weight. After ball milling the cyclohexane solvent was then removed by evaporation and the resulting grey solid was dried at 110° C. The mean crystallite size of the precursor after ball milling was found to be about 350 Å as measured by X-ray diffractometry. A portion of the ball milled precursor was pelleted, ground, sieved to give particles 500–710μ in size, charged to a reactor and calcined in situ as described in Example 1. for 110 hours. With a butane feed concentration of 17.5 mole % and an inlet oxygen concentration of 17.3 mole % (remainder inerts) at a reactor temperature of 360° C. and GHSV 965 hr$^{-1}$ the catalyst gave an n-butane conversion of 15% and a selectivity to maleic anhydride of 75 mole %. The surface area of the final catalyst was 30 m²/g.

EXAMPLE 17

A vanadium/phosphorus catalyst precursor was prepared, boiled in water, washed with warm water, dried, ball milled in the presence of a solvent and dispersant, dried, pelleted, crushed and sieved to give particles 500–700μ in size as described in Example 1. After ball milling as described in Example 1 the catalyst precursor had a mean crystallite size of about 250 Å as measured by X-ray diffractometry. A portion of the particles (5.0 mls) was then loaded to a fixed bed tubular reactor and the catalyst was calcined in situ by heating to 385° C. at a rate of 9° C./min. whilst a 1.5% v/v n-butane/air mixture flowed through the bed at a GHSV of 1000 hr$^{-1}$. After 235 hours time on line a gas stream similar to the feed gases of a recycle process was fed to the reactor (20.3 mole % n-butane, 18.9 mole % oxygen, 31.6 mole % CO, 29.2 mole % $CO_2$). At a reactor temperature of 360° C. and GHSV 1000 hr$^{-1}$ the catalyst gave an n-butane conversion of about 9% and a selectivity to maleic anhydride of about 80 mole %. The surface area of the final catalyst was 38 m²/g.

EXAMPLE 18

Catalyst A

A catalyst was prepared in the following manner:

Vanadium pentoxide (303 g) and concentrated hydrochloric acid (41) were charged into a 5 l flask. The mixture was heated to boiling with stirring, anf refluxed at atmospheric pressure for 2 hours. Phosphoric acid (88%, 225 mls) was added with stirring and the mixture refluxed for a further 2 hours. At the end of this period 3.2 l of liquid were removed by side-arm distillation. Concentrated hydrochloric acid (1 l) was added to the residue which was refluxed for 1 hour. The product was then evaporated to dryness to give a catalyst precursor which was dried in an air oven. The resultant mass was boiled with water (20 ml per gram of solid), filtered and dried in an air oven.

A portion of the mixture was ballmilled in cyclohexane in the presence of oleylamine as a dispersant (2% by weight of catalyst) and molybdenum trioxide ($MoO_3$) to give a catalyst precursor having an atomic ratio V:P:Mo of approximately 1:1:0.02.

The resultant solid was collected, dried and pelleted with a pelleting agent sold under the trade name "Sterotex" (3% wt/wt) using a pressure of 16 tons in $^{-2}$. The tablet was crushed and sieved to give particles of the size 500–710$\mu$.

A portion of the catalyst was charged into a tubular fixed-bed reactor.

Catalyst B

A catalyst was prepared in the following manner:

Vanadium pentoxide (60.6 g) and concentrated aqueous hydrochloric acid (790 ml) were refluxed with stirring for one hour. To this solution orthophosphoric acid (88% 50.9 ml) was added and the solution refluxed for a further hour. A portion of solvent (600 ml) was then removed by side arm distillation and a further 200 ml of concentrated aqueous hydrochloric acid was added. The resulting solution was refluxed for a further period of about 1½ hours. The solution was then evaporated to dryness and the resulting solid dried in an oven at 115° C. The resulting solid was boiled with water (20 mls/g solid) for about 2½ hours and the resulting suspension was filtered hot, washed with a small amount of warm water and dried in an air oven. A portion of the dried solid was then ball milled in cyclohexane in the presence of 2% by weight of the solid of an organic comb graft copolymer (poly 12-hydroxystearic acid (molecular weight about 1800)/ethyl acrylate/dimethyl aminoethyl methacrylate:50/45/5) for 144 hours. The grey solid was recovered and dried at about 90° C. A portion of this was mixed with a pelleting agent sold under the trade name "Sterotex" (3% by weight) and pelletised under a pressure of 16 tons in $^{-2}$. The pellet was crushed to give granules of size 500–710$\mu$. The particles were dried at 150° C. and were then impregnated with an isobutanol solution containing lanthanum nitrate as $La(NO_3)_3.6H_2O$ (14 g per 100 ml) to give a catalyst with La:V ratio 0.027:1. After drying, a portion was charged in to a tubular fixed bed reactor.

Both catalyst were activated in a similar manner as follows. The activation period was approximately 100 hours.

Each catalyst was calcined in situ by heating at 380° C. at a rate of 9° C./min whilst a 1.5 v/v n-butane/air mixture flowed through the bed at a gas hourly space velocity (GHSV) of 1000 hr$^1$.

Maleic anhydride was then produced as follows: A gaseous feed comprising butane, oxygen and an inert gas (substantially all nitrogen) was passed over the catalyst. The exit gases from the reactor were analysed for unreacted butane, carbon oxides, maleic acid and anhydride, and higher acids (e.g. acetic and acrylic acids). Data are presented in the table 3.

TABLE 3

| | BUTANE FED Mol % | OXYGEN FED Mol % | INERT FED Mol % | GHSV hr$^{-1}$ | TEMP °C. | C$_4$ CONVERSION Mol % | SEL Mol % | ACTIVITY Mol MA/liter catalyst/hr |
|---|---|---|---|---|---|---|---|---|
| CATALYST A | 12.0 | 16.3 | 71.7 | 2000 | 380 | 14 | 70 | 0.98 |
| | 13.4 | 16.0 | 70.6 | 1000 | 370 | 18 | 61 | 0.61 |
| CATALYST B | 12.6 | 16.2 | 71.2 | 2000 | 379 | 12 | 72 | 0.91 |

GHSV means gas hourly space velocity
SEL means selectivity to MA based on butane converted.
MA means the total of maleic anhydride and maleic acid expressed as anhydride.

We claim:

1. A process for producing maleic anhydride which comprises oxidising 10 to 50% of a hydrocarbon which comprises at least 4 linear carbon atoms by contacting it with oxygen, the hydrocarbon concentration being greater than 10 molar percent and being higher than the flammable limit, the oxygen concentration being greater than 13 molar percent and the concentration of inert gas being greater than 70 molar percent of the total material fed to the reaction, in the presence of a catalyst which consists essentially of a phosphorus/vanadium mixed oxide, the atomic ratio of vanadium to phosphorus being in the range 0.5:1 to 2:1, the surface area of the catalyst being at least 10 sq meters per gram.

2. A process as claimed in claim 1 in which the hydrocarbon is a linear C$_4$ hydrocarbon.

3. A process as claimed in claim 2 in which the oxygen concentration is 14 to 20 molar percent.

4. A process as claimed in claim 2 in which the phosphorus/vanadium mixed oxide catalyst includes a promoter.

5. A process as claimed in claim 1 in which the phosphorus/vanadium mixed oxide catalyst is supported on a catalyst support.

6. A process as claimed in claim 1 in which the catalyst is present as a fixed bed.

* * * * *